US00PP26741P3

(12) United States Plant Patent
Klemm et al.

(10) Patent No.: US PP26,741 P3
(45) Date of Patent: May 17, 2016

(54) ***DAHLIA* PLANT NAMED 'KLEDH13033'**

(50) Latin Name: ***Dahlia* sp.**
Varietal Denomination: KLEDH13033

(71) Applicant: Klemm+Sohn GmbH & Co. KG, Stuttgart (DE)

(72) Inventors: Nils Klemm, Stuttgart (DE); Silke Wagener, Leinfelden-Echterdingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 144 days.

(21) Appl. No.: 14/120,257

(22) Filed: May 13, 2014

(65) Prior Publication Data

US 2015/0334900 P1 Nov. 19, 2015

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — Keith Robinson

(74) *Attorney, Agent, or Firm* — James M. Weatherly; Bethany R. Roahrig; Cochran Freund & Young, LLC

(57) ABSTRACT

A new *Dahlia* plant particularly distinguished by having yellow ray florets with a pink eye and compact, semi-upright, freely basal branching inflorescences held above the foliage, is disclosed.

1 Drawing Sheet

Genus and species: *Dahlia* sp.
Variety denomination: 'KLEDH13033'.

BACKGROUND OF THE NEW PLANT

The present invention comprises a new and distinct variety of *Dahlia*, botanically known as *Dahlia* sp. and hereinafter referred to by the variety name 'KLEDH13033'. 'KLEDH13033' is a selection that results from an open pollination of unknown parents in the summer of 2008. Seed were collected from the open pollination and planted, with a single plant named 'KLEDH13033' discovered in Stuttgart, Germany in May of 2009. Initial unrooted cuttings of 'KLEDH13033' were taken in May of 2009. 'KLEDH13033' was found to reproduce true to type in successive generations of asexual propagation via unrooted cuttings in Stuttgart, Germany.

SUMMARY

The following are the most outstanding and distinguishing characteristics of this new variety when grown under normal horticultural practices in Stuttgart, Germany.

1. Yellow ray florets with a red eye; and
2. Compact, semi-upright, freely basal branching inflorescences held above the foliage.

CROSS REFERENCE TO RELATED APPLICATIONS

Plant Breeder's Rights for 'KLEDH13033' were applied for in Canada on Jan. 9, 2014, application number 14-8172. 'KLEDH13033' has not been made publicly available or sold more than one year prior to the filing date of this application.

DESCRIPTION OF THE PHOTOGRAPHS

This new *Dahlia* plant is illustrated by the accompanying photographs which show an overall view of the plant. The colors shown are as true as can be reasonably obtained by conventional photographic procedures.

DESCRIPTION OF THE NEW VARIETY

Figure 1:
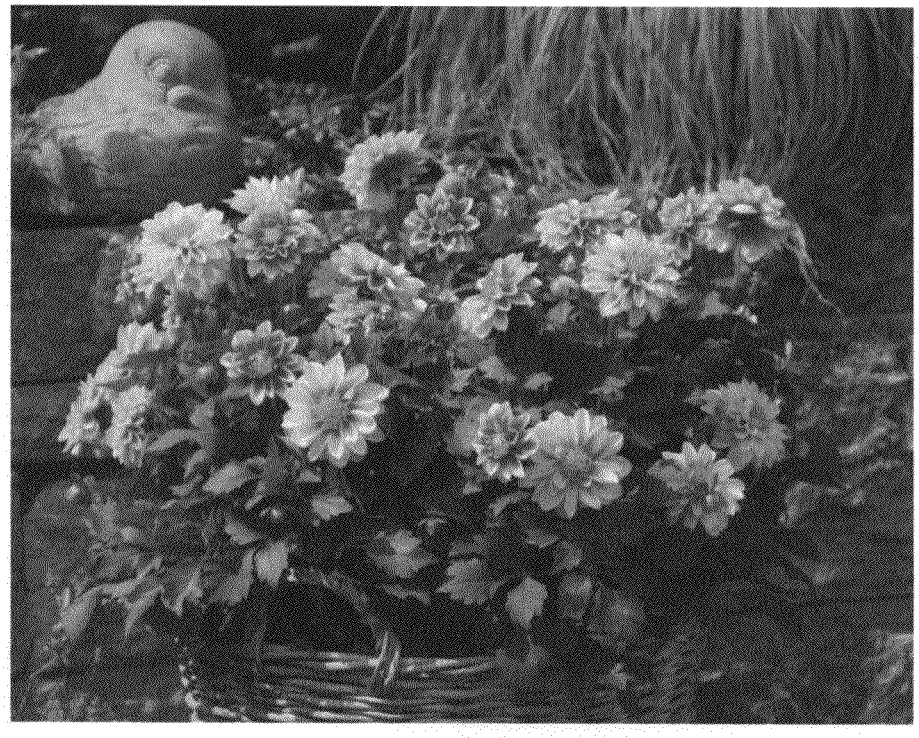
FIG. 1 shows the overall plant habit of the plant grown in a basket. The plant is about 5 months-old grown in Stuttgart, Germany in May 2013.
Figure 2:
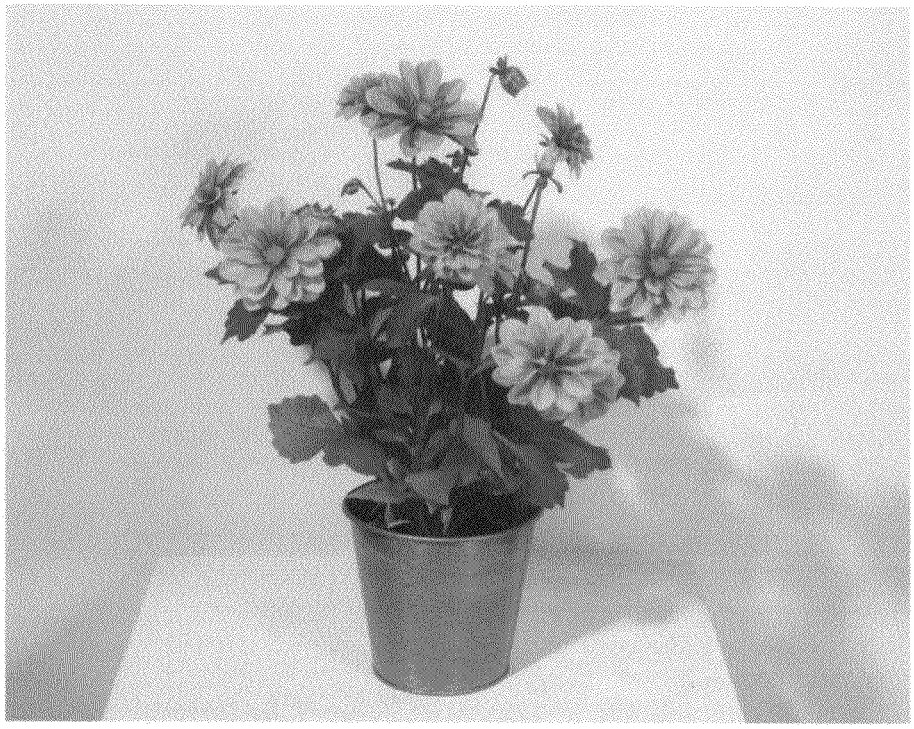
FIG. 2 shows the overall plant habit of the plant grown in a pot. The plant is about 3 months-old grown in Stuttgart, Germany in July 2013.

The following detailed descriptions set forth the distinctive characteristics of 'KLEDH13033'. The data which define these characteristics were collected from asexual reproductions carried out in Stuttgart, Germany. Data was collected on four month-old plants grown indoors, under natural and artificial light in Stuttgart, Germany in January of 2014. Plants were pinched one time with a growth regulator. Color references are to The R.H.S. Colour Chart of The Royal Horticultural Society of London (R.H.S.), $5^{th}$ edition (2007).

Classification:

*Family*.—Asteraceae.
*Species*.—*Dahlia* sp.
*Common name*.—*Dahlia*.
*Variety*.—'KLEDH13033'.

Parentage: Unknown.

Propagation:

*Type*.—Asexual, unrooted cuttings.
*Time to produce a rooted young plant*.—3 to 4 weeks.
*Root description*.—Medium thickness, light tan (RHS 155A) in colour.
*Rooting habit*.—Freely branching, moderately dense.
*Time for root initiations*.—About 2 weeks; to produce a rooted young plant 3-4 weeks.

Plant description:

*Plant and growth habit.*—Compact, semi-upright, freely basal branching inflorescences held above the foliar plant.

*Plant height.*—25.0 cm.

*Plant diameter.*—35.0 cm.

Lateral branches:

*Length.*—About 15.0 cm.

*Diameter.*—About 1.0 cm.

*Stem and lateral branch color.*—Between RHS 143C and RHS 144B with an anthocyanin of RHS 183C.

*Internode length.*—About 1.0 cm to 2.0 cm.

*Aspect.*—About 30° from vertical.

*Strength.*—Strong.

*Texture.*—Smooth.

Foliage description:

*Arrangement.*—Leaves opposite, three or five leaflets.

*Leaf type.*—Pinnate.

*Glossiness.*—Upper surface: Matt and glossy. Lower surface: Matt.

*Length.*—Up to 15.0 cm.

*Width.*—About 13.0 cm.

*Shape.*—Ovate.

*Apex.*—Acute to obtuse.

*Base.*—Acute to obtuse.

*Margin.*—Moderately serrated.

*Venation pattern.*—Pinnate.

*Venation color.*—RHS 139B.

*Texture.*—Both upper and lower surfaces: Pilose.

*Color.*—Both immature and mature: Upper surface: RHS 139A. Lower surface: RHS N138C.

Petioles:

*Length.*—2.0 cm until the first leaflet pair, 3 to 5 cm till the second leaflet pair.

*Diameter.*—About 0.7 cm.

*Texture.*—Upper and lower surfaces: Smooth.

*Color.*—Upper and lower surfaces: RHS 138B.

Inflorescence description:

*Appearance and arrangement.*—Daisy-eyed double inflorescences above the foliar plant.

*Attitude of flower head.*—Semi-upright.

*Fragrance.*—Absent.

*Time to flower.*—Winter: About 3 months after planting. Summer: About 2 months after planting.

*Post-production longevity.*—Flower continuously during summer and autumn.

Inflorescence bud:

*Height.*—About 1.0 cm.

*Diameter.*—1.0 to 1.5 cm.

*Shape.*—Oblate.

*Color.*—RHS 144B and RHS 144A towards the base.

Inflorescence size:

*Diameter.*—About 10.0 cm.

*Depth (height).*—About 5.0 cm.

*Disc diameter.*—About 2.0 cm.

*Receptacle height.*—1.5 to 2.0 cm.

*Receptacle diameter.*—4.0 cm.

*Receptacle color.*—RHS 141B.

Ray florets:

*Quantity per inflorescence.*—About 50 arranged in 3 to 4 whorls.

*Length.*—About 3.5 cm.

*Width.*—About 2.5 cm.

*Shape.*—Elliptical.

*Apex.*—Acute to obtuse.

*Base.*—Acute.

*Margin.*—Entire.

*Aspect.*—Semi-upright.

*Texture.*—Upper to lower surface: Smooth.

*Color.*—Immature: Upper surface: RHS 9A and RHS 45B. Lower surface: RHS 9B and RHS 45C. Mature: Upper surface: RHS 9A and RHS 42A basal. Lower surface: RHS 9B and RHS 42B basal.

Disc florets:

*Quantity per inflorescence.*—About 60.

*Length.*—About 1.0 cm.

*Diameter.*—0.1 cm.

*Shape.*—Tubular.

*Apex.*—Rounded.

*Texture.*—Inner and outer surfaces: Smooth.

*Color.*—Immature and mature: Inner and outer surfaces: RHS 12B. Mature: Inner and outer surfaces: RHS 12B.

Phyllaries:

*Quantity per inflorescence.*—9.

*Length.*—2.0 cm.

*Width.*—1.0 cm.

*Shape.*—Oblong.

*Apex.*—Obtuse.

*Base.*—Truncase.

*Margin.*—Absent.

*Texture.*—Upper and lower surfaces: Smooth.

*Color.*—Upper and lower surfaces: RHS 144B basal, RHS 144D apex.

Peduncles:

*Length, terminal peduncle.*—9.0 cm.

*Length, axillary peduncle.*—6.0 cm.

*Diameter.*—0.4 cm.

*Aspect.*—Semi-upright.

*Strength.*—Strong.

*Texture.*—Smooth.

*Color.*—RHS 143B.

Reproductive organs:

*Androecium.*—Only full developed on disc florets. Quantity per floret: 4. Filament length: 0.3 cm. Filament color: RHS 3B. Anther shape: Lanceolate. Anther length: 0.5 cm. Anther color: RHS 15A. Pollen amount: Abundant. Pollen color: RHS 21A.

*Gynoecium.*—Quantity per floret: 1. Pistil length: 1.5 cm. Style length: 0.9 cm. Style color: RHS 1D. Stigma shape: Lanceolate pinnate. Stigma color: RHS 13A. Ovary color: RHS 154C.

*Fruit and seed set.*—No fruit and seed set observed to date.

Disease and insect/pest resistance: No special observations were made.

COMPARISON WITH KNOWN VARIETY

'KLEDH13033' is most similar to the commercial *Dahlia* plant named 'KLEDH11031' commercially known as 'Yogi' (U.S. Plant Pat. No. 25,295). Differences between the two varieties are described in Table 1:

TABLE 1

Comparison with Known Variety

| Trait | Variety 'KLEDH13033' | Commercial line 'KLEDH11031' |
|---|---|---|
| Ray florets color | Yellow with a red eye | Pink with purple/red eye |

We claim:

1. A new and distinct variety of *Dahlia* plant named 'KLEDH13033' as illustrated and described herein.

* * * * *